(12) United States Patent
Otaki et al.

(10) Patent No.: US 10,222,341 B2
(45) Date of Patent: Mar. 5, 2019

(54) FOCUSING APPARATUS, FOCUSING METHOD, AND PATTERN INSPECTION METHOD

(71) Applicant: NuFlare Technology, Inc., Yokohama-shi (JP)

(72) Inventors: Toshiaki Otaki, Yokohama (JP); Riki Ogawa, Kawasaki (JP)

(73) Assignee: NuFlare Technology, Inc., Yokohama-shi (JP)

( * ) Notice: Subject to any disclaimer, the term of this patent is extended or adjusted under 35 U.S.C. 154(b) by 43 days.

(21) Appl. No.: 15/634,517

(22) Filed: Jun. 27, 2017

(65) Prior Publication Data

US 2018/0003649 A1    Jan. 4, 2018

(30) Foreign Application Priority Data

Jul. 1, 2016    (JP) .................................. 2016-131993

(51) Int. Cl.
*H04N 7/18*    (2006.01)
*H04N 5/232*    (2006.01)
(Continued)

(52) U.S. Cl.
CPC ..... *G01N 21/95607* (2013.01); *H04N 5/2352* (2013.01); *H04N 5/23212* (2013.01); *G01N 2021/95676* (2013.01); *H04N 5/372* (2013.01)

(58) Field of Classification Search
CPC .......... H04N 7/18; H04N 7/181; H04N 7/183; H04N 5/23212; H04N 5/2352;
(Continued)

(56) References Cited

U.S. PATENT DOCUMENTS 9,423,356 B2 *    8/2016    Ogawa ............. G01N 21/95607

FOREIGN PATENT DOCUMENTS

JP    2012-211834    11/2012
JP    2014-228670    12/2014
(Continued)

OTHER PUBLICATIONS

Korean Office Action dated Sep. 17, 2018 in Korean Application No. 10-2017-0081692, with English translation, 11 pages.

*Primary Examiner* — Sherrie Hsia
(74) *Attorney, Agent, or Firm* — Oblon, McClelland, Maier & Neustadt, L.L.P.

(57) ABSTRACT

A focusing apparatus includes a first reticle, arranged at the front side of a conjugate position of a TDI sensor; a second reticle, arranged at the back side of the conjugate position; an equalizing circuit to perform gray scale value equalization by using a gray scale value output by the TDI sensor which received the pattern image by illumination light not passing through the first and second reticles; and a distance change/move amount calculation circuit to calculate, in a state where the gray scale value equalization has been performed, a distance change/move amount of a relative distance, for focusing the pattern image of the substrate, between the substrate and the conjugate position of the TDI sensor by using a first derivative value of a gray scale value output by the TDI sensor which received the pattern image by the reflection illumination light having passed through the first and second reticles.

10 Claims, 12 Drawing Sheets

(51) Int. Cl.
*H04N 5/235* (2006.01)
*G01N 21/956* (2006.01)
*H04N 5/372* (2011.01)

(58) Field of Classification Search
CPC ........ H04N 5/372; H04N 5/232; H04N 5/235;
G01N 21/95607; G01N 2021/95676;
G06T 7/0004; G06T 2207/30148; G06T
2207/30164
USPC ..... 348/95, 94, 61, 129, 130, 125, 133, 142;
382/141, 151, 152; 702/34; 356/239.1,
356/237.1, 237.2
See application file for complete search history.

(56) References Cited

FOREIGN PATENT DOCUMENTS

| | | |
|---|---|---|
| KR | 10-2015-0130919 | 11/2015 |
| KR | 10-2006-0043037 | 5/2016 |

\* cited by examiner

TDI Accumulation Direction

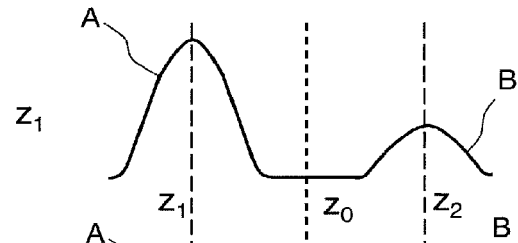
FIG.10A
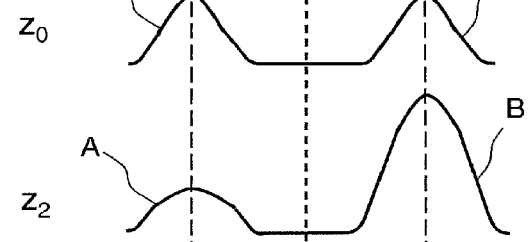
FIG.10B
FIG.10C
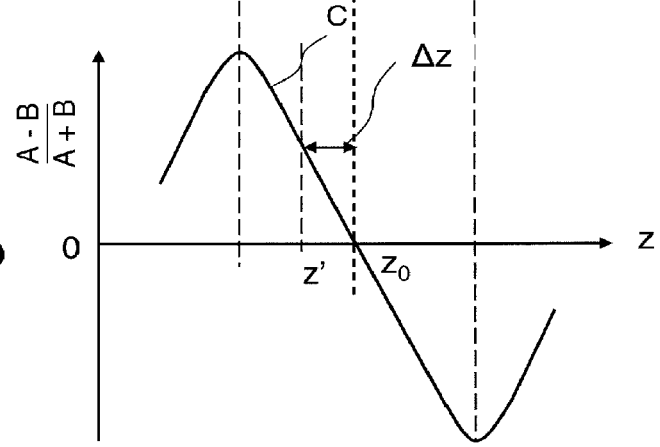
FIG.10D

FOCUSING APPARATUS, FOCUSING METHOD, AND PATTERN INSPECTION METHOD

CROSS-REFERENCE TO RELATED APPLICATION

This application is based upon and claims the benefit of priority from the prior Japanese Patent Application No. 2016-131993 filed on Jul. 1, 2016 in Japan, the entire contents of which are incorporated herein by reference.

BACKGROUND OF THE INVENTION

Field of the Invention

Embodiments of the present invention relate generally to a focusing apparatus, focusing method, and pattern inspection method. For example, embodiments of the present invention relate to a pattern inspection technique for inspecting pattern defects of an object serving as a target workpiece or "sample" used in manufacturing semiconductor devices, and to an inspection apparatus for inspecting an exposure mask substrate used in manufacturing semiconductor elements or liquid crystal displays (LCDs).

Description of Related Art

In recent years, with the advance of high integration and large capacity of large-scale integration (LSI) circuits, the line width (critical dimension) required for circuits of semiconductor elements is becoming progressively narrower. Such semiconductor elements are manufactured by circuit formation of exposing and transferring a pattern onto a wafer by means of a reduced projection exposure apparatus known as a stepper while using an original or "master" pattern (also called a mask or a reticle, hereinafter generically referred to as a mask) with a circuit pattern formed thereon. Then, in fabricating a mask for transfer printing such a fine circuit pattern onto a wafer, a pattern writing apparatus capable of writing or "drawing" fine circuit patterns by using electron beams needs to be employed. Pattern circuits may be written directly on the wafer by the pattern writing apparatus. Also, a laser beam writing apparatus that uses laser beams in place of electron beams for writing a pattern is under development.

Meanwhile, the LSI manufacturing requires a tremendous amount of manufacturing cost, therefore it is crucial to improve its yield. However, as typified by a 1-gigabit DRAM (Dynamic Random Access Memory), the scale of patterns configuring an LSI has become on the order of nanometers from submicrons. One of major factors that decrease the yield of the LSI manufacturing is due to pattern defects on the mask used for exposing and transfer printing an ultrafine pattern onto a semiconductor wafer by the photolithography technology. In recent years, with miniaturization of dimensions of LSI patterns formed on a semiconductor wafer, dimension to be detected as a pattern defect has become extremely small. Therefore, the pattern inspection apparatus for inspecting defects of the transfer mask used in manufacturing LSI needs to be highly accurate.

As an inspection method, there is known a method of comparing an optical image obtained by imaging, at a predetermined magnification, a pattern formed on a target object or "sample" such as a lithography mask by using a magnification optical system with design data or an optical image obtained by imaging the same pattern on the target object. For example, the methods described below are known as pattern inspection methods: the "die-to-die inspection" method that compares data of optical images of identical patterns at different positions on the same mask; and the "die-to-database inspection" method that inputs, into an inspection apparatus, writing data (design pattern data) generated by converting pattern-designed CAD data to a writing apparatus specific format to be input to the writing apparatus when a pattern is written on the mask, generates a design image (reference image) based on the input writing data, and compares the generated design image with an optical image (serving as measured target data) obtained by imaging the pattern. In such inspection methods for use in the inspection apparatus, a target object is placed on the stage so that a light flux may scan the target object as the stage moves in order to perform an inspection. Specifically, the target object is irradiated with a light flux from the light source through the illumination optical system. Light transmitted through the target object or reflected therefrom forms an image on a sensor through the optical system. The image captured by the sensor is transmitted as measured target data to the comparison circuit. After performing position adjustment of images, the comparison circuit compares the measured target data with reference data in accordance with an appropriate algorithm, and determines that there exists a pattern defect if the compared data are not identical.

For inspecting defects of an inspection target substrate, such as a mask, it is required to precisely match the position of the surface of the target to be inspected with the sensor position. It has been disclosed that, after illumination light has been incident on the first mask and the second mask in this order, a pattern image of the first mask is formed at the front side of the pattern surface of the substrate to be inspected, and a pattern image of the second mask is formed at the back side of the pattern surface of the substrate to be inspected, and adjustment of the focus position is performed based on a difference value between the contrast of the pattern image of the first mask and the contrast of the pattern image of the second mask which are formed on the sensor due to reflection from the pattern surface of the inspection substrate (e.g., refer to Japanese Patent Application Laid-open No. 2014-228670). However, in a projection system in which a reticle image is projected from a reflective illumination system, if reflectance varies depending on a pattern formed on the surface of the projected inspection substrate, there is a problem in that accurate focusing is difficult.

BRIEF SUMMARY OF THE INVENTION

According to one aspect of the present invention, a focusing apparatus includes a reflection illumination optical system configured to illuminate a substrate, on which a pattern is formed, with a reflection illumination light; an image forming optical system configured to form a pattern image of the substrate; a time delay integration sensor (TDI sensor) configured to receive the pattern image of the substrate; a first reticle, arranged at a front side of a conjugate position of the TDI sensor facing a surface of the substrate, along an optical axis direction, in an optical path of the reflection illumination optical system, configured to be irradiated with the reflection illumination light, and have thereon a light-shielding pattern whose end part is parallel with a direction of time integration of the TDI sensor, and a transmission pattern whose occupancy rate in an illumination region is larger than that of the light-shielding pattern; a second reticle, arranged at a back side of the conjugate position of the TDI sensor facing the surface of the substrate, to be equivalently opposite to the first reticle, along the optical axis direction, in the optical path of the reflection illumination optical system, configured to be irradiated with the reflection illumination light, and have thereon a light-shielding pattern and a transmission pattern which are same shapes as those of the first reticle and whose arrangement direction is opposite to that of the first reticle; an equalizing circuit configured to perform gray scale value equalization by using a gray scale value output by the TDI sensor which received the pattern image of the substrate generated by irradiating the substrate with the reflection illumination light not passing through the first and second reticles; a distance change/move amount calculation circuit configured to calculate, in a state where the gray scale value equalization has been performed, a distance change/move amount of a relative distance, for focusing the pattern image of the substrate, between the substrate and the conjugate position of the TDI sensor by using a first derivative value of a gray scale value output by the TDI sensor which received the pattern image of the substrate generated by irradiating the substrate with the reflection illumination light having passed through the first and second reticles; and a drive mechanism configured to change/move the relative distance between the substrate and the conjugate position of the TDI sensor by using the distance change/move amount.

According to another aspect of the present invention, a focusing method includes illuminating a substrate, on which a pattern is formed, with a reflection illumination light by using a reflection illumination optical system; receiving a pattern image of the substrate by a time delay integration sensor (TDI sensor) through an image forming optical system which forms the pattern image of the substrate; performing gray scale value equalization by using a gray scale value output by the TDI sensor which received the pattern image of the substrate generated by irradiating the substrate with the reflection illumination light; receiving the pattern image of the substrate by the TDI sensor generated by irradiating the substrate with the reflection illumination light having passed through a first reticle and a second reticle, in a state where the gray scale value equalization has been performed, by using the first and second reticles, the first reticle being arranged at a front side of a conjugate position of the TDI sensor facing a surface of the substrate, along an optical axis direction, in an optical path of the reflection illumination optical system, being configured to be irradiated with the reflection illumination light, and having thereon a light-shielding pattern whose end part is parallel with a direction of time integration of the TDI sensor, and a transmission pattern whose occupancy rate in an illumination region is larger than that of the light-shielding pattern, and the second reticle, being arranged at a back side of the conjugate position of the TDI sensor facing the surface of the substrate, to be equivalently opposite to the first reticle, along the optical axis direction, in the optical path of the reflection illumination optical system, being configured to be irradiated with the reflection illumination light, and having thereon a light-shielding pattern and a transmission pattern which are same shapes as those of the first reticle and whose arrangement direction is opposite to that of the first reticle; calculating, in the state where the gray scale value equalization has been performed, a distance change/move amount of a relative distance, for focusing the pattern image of the substrate, between the substrate and the conjugate position of the TDI sensor by using a first derivative value of a gray scale value output by the TDI sensor which received the pattern image of the substrate generated by irradiating the substrate with the reflection illumination light having passed through the first and second reticles; and changing/moving the relative distance between the substrate and the conjugate position of the TDI sensor by using the distance change/move amount.

According to yet another aspect of the present invention, a pattern inspection method includes illuminating a substrate, on which an alignment pattern and a circuit pattern are formed, with a reflection illumination light by using a reflection illumination optical system; receiving an alignment pattern image of the substrate by a time delay integration sensor (TDI sensor) through an image forming optical system which forms a pattern image of the substrate; performing gray scale value equalization by adjusting a gain and offset by using a gray scale value output by the TDI sensor which received the alignment pattern image of the substrate generated by irradiating the substrate with the reflection illumination light; arranging a first reticle, where a light-shielding pattern whose end part is parallel with a direction of time integration of the TDI sensor, and a transmission pattern whose occupancy rate in an illumination region is larger than that of the light-shielding pattern are formed, at a front side of a conjugate position of the TDI sensor facing a surface of the substrate, along an optical axis direction, in an optical path of the reflection illumination optical system, and also arranging a second reticle, where a light-shielding pattern and a transmission pattern which are same shapes as those of the first reticle and whose arrangement direction is opposite to that of the first reticle, at a back side of the conjugate position of the TDI sensor facing the surface of the substrate, to be equivalently opposite to the first reticle, along the optical axis direction, in the optical path of the reflection illumination optical system; measuring, in a state where the gray scale value equalization has been performed by adjusting the gain and offset, a height position of the substrate by using a first derivative value of a gray scale value output by the TDI sensor which received the alignment pattern image of the substrate generated by irradiating the substrate with the reflection illumination light having passed through the first and second reticles; acquiring a height position distribution of the substrate, based on the height position of the substrate; and inspecting the circuit pattern formed on the substrate while changing the height position of the substrate, based on the height position distribution.

BRIEF DESCRIPTION OF THE DRAWINGS

FIGS. 10A to 10D show examples of a relation between a first derivative value of a gray scale value and a focus position according to the first embodiment;

DETAILED DESCRIPTION OF THE INVENTION

Embodiments of the present invention describe a focusing apparatus, a focusing method, and a pattern inspection method, which can perform focusing highly accurately irrespective of patterns formed on the inspection substrate surface where a reticle image is projected.

First Embodiment

Figure 1:
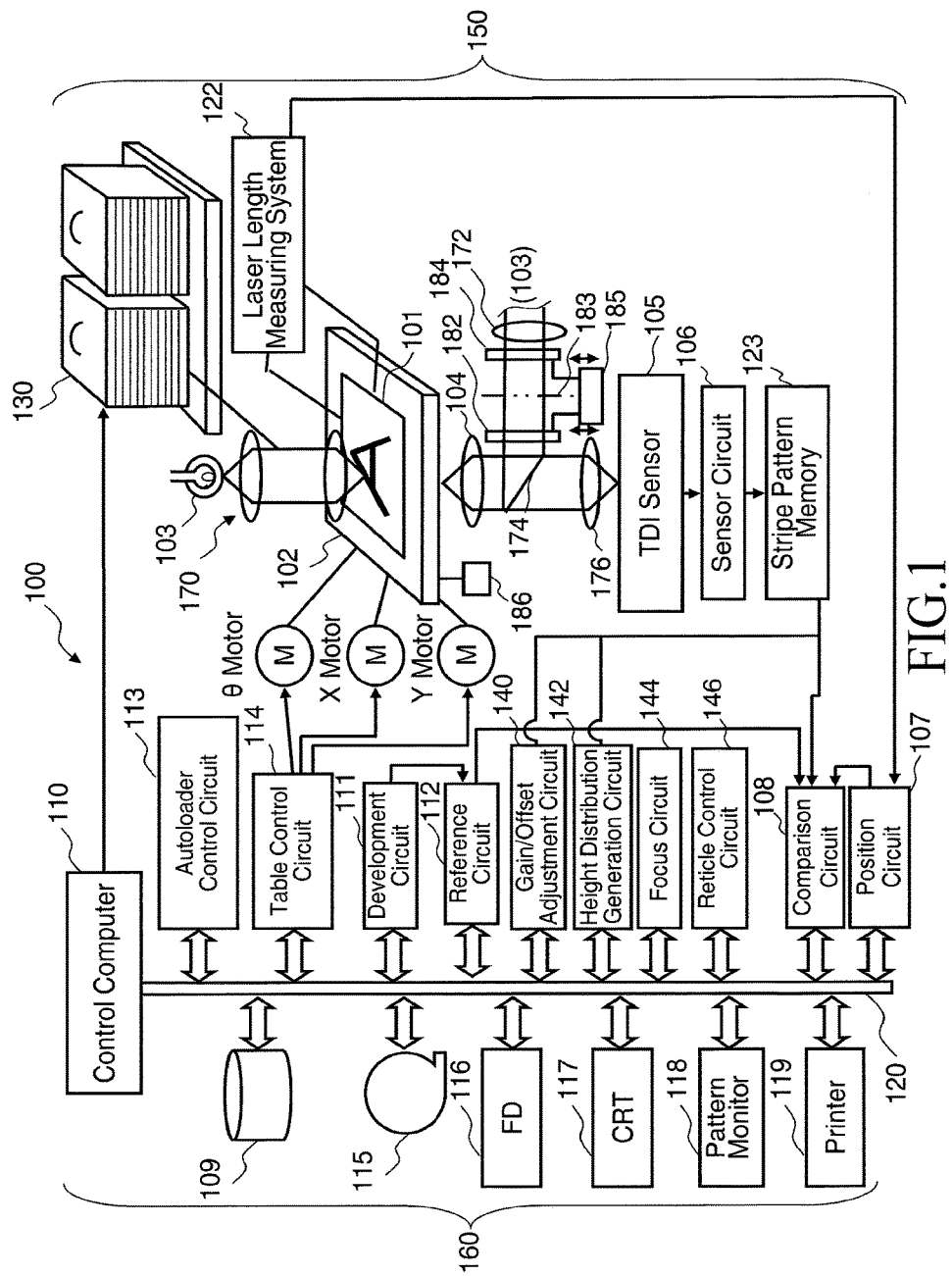
FIG. 1 illustrates a configuration of a pattern inspection apparatus according to a first embodiment.

FIG. 1 illustrates a configuration of a pattern inspection apparatus according to a first embodiment. As shown in FIG. 1, an inspection apparatus 100 that inspects defects of a pattern formed on a mask substrate 101 (example of inspection substrate) includes an optical image acquisition unit 150 and a control system circuit 160 (control circuit).

The optical image acquisition unit 150 includes a light source 103, a transmission illumination optical system 170, an XYθ table 102 arranged movably, an objective lens 104, a beam splitter 174, a reflection illumination optical system 172, an image forming optical system 176, reticles 182 and 184, a reticle drive mechanism 185, a TDI (Time Delay Integration) sensor 105, a sensor circuit 106, a stripe pattern memory 123, and a laser length measuring system 122. On the XYθ table 102, there is placed a mask substrate 101 (example of inspection substrate) transmitted from a cassette 130. The mask substrate 101 is, for example, an exposure photomask used for transfer printing a pattern onto a wafer. On the photomask, there are formed a pattern composed of a plurality of figure patterns to be inspected, and a plurality of alignment patterns. The mask substrate 101, for example, with its pattern forming surface facing downward, is arranged on the XYθ table 102.

In the control system circuit 160, a control computer 110 is connected, through a bus 120, to a position circuit 107, a comparison circuit 108, a development circuit 111, a reference circuit 112, an autoloader control circuit 113, a table control circuit 114, a gain/offset adjustment circuit 140, a height distribution generation circuit 142, a focus circuit 144, a reticle control circuit 146, a magnetic disk device 109, a magnetic tape device 115, a flexible disk device (FD) 116, a CRT 117, a pattern monitor 118, and a printer 119. The sensor circuit 106 is connected to the stripe pattern memory 123 which is connected to the comparison circuit 108. The XYθ table 102 is driven by the motors of the X-axis, Y-axis, and θ-axis. The reflection illumination optical system 172 includes the objective lens 104 and the beam splitter 174.

In the inspection apparatus 100, an inspection optical system with large magnification is composed of the light source 103, the transmission illumination optical system 170, the XYθ table 102 arranged movably, the objective lens 104, the beam splitter 174, the reflection illumination optical system 172, the image forming optical system 176, the reticles 182 and 184, the TDI sensor 105, and the sensor circuit 106. For example, an inspection optical system with magnification of 200 to 300 times is configured.

The XYθ table 102 is driven by the table control circuit 114 under the control of the control computer 110. The XYθ table 102 can be moved by a drive system such as a three-axis (X, Y, and θ) motor, which drives the table in the directions of x, y, and θ. For example, a linear motor can be used as each of these X, Y, and θ motors. The XYθ table 102 is movable in the horizontal direction and the rotation direction by the motors of the X-, Y-, and θ-axis. The XYθ table 102 is adjusted to the focus position (optical axis direction: Z axis direction) where an image of the pattern forming surface of the mask substrate 101 is focused on the TDI sensor 105, by the focus circuit 144 under the control of the control computer 110. For example, the focus position is adjusted by a movement of the XYθ table 102 in the optical axis direction (Z axis direction) by the drive mechanism 186 driven by the focus circuit 144. It is preferable to use a piezoelectric element 142 as the drive mechanism 186. The movement position of the mask substrate 101 placed on the XYθ table 102 is measured by the laser length measuring system 122, and supplied to the position circuit 107.

Design pattern data (writing data) used as the basis of forming patterns on the mask substrate 101 and alignment mark data are input from the outside of the inspection apparatus 100, and stored in the magnetic disk device 109.

FIG. 1 shows configuration elements necessary for describing the first embodiment. It should be understood that other configuration elements generally necessary for the inspection apparatus 100 may also be included therein.

Figure 2:
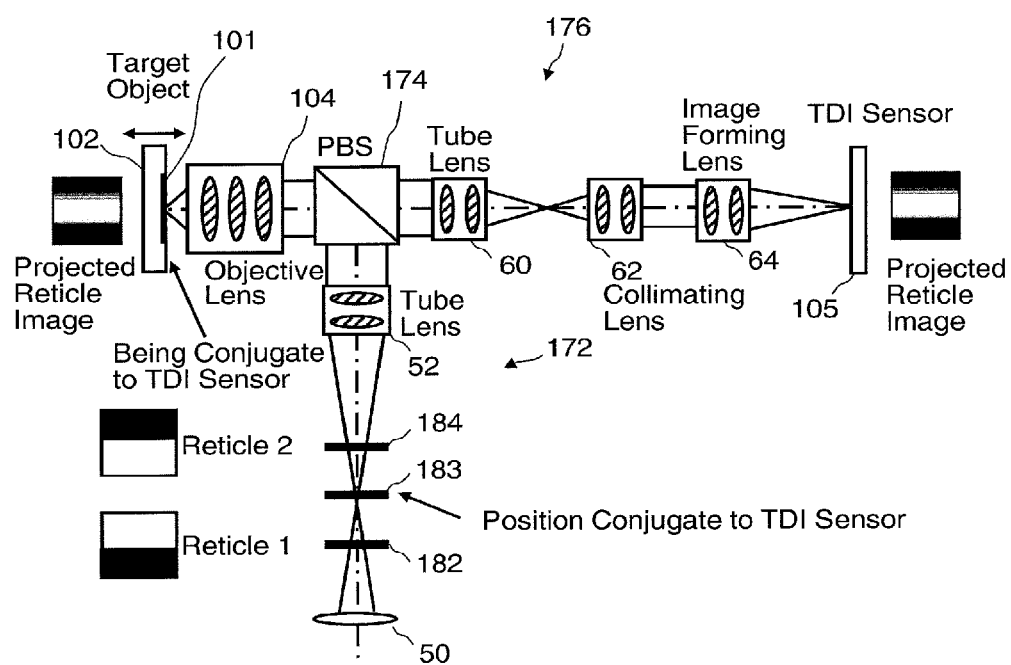
FIG. 2 shows an example of configuration of an optical system of an inspection apparatus according to the first embodiment.

FIG. 2 shows an example of configuration of an optical system of an inspection apparatus according to the first embodiment. In FIG. 2, there is generated a laser light (e.g., DUV light) being an inspection light from the light source 103, whose wavelength is equal to or shorter than that of the ultraviolet region. A part of the generated light is divided into a light for transmission illumination and a light for reflection illumination by a beam splitter, etc. (not shown). In the first embodiment, a focus position is adjusted by using an illumination light for reflection (reflection illumination light). Therefore FIG. 2 shows a configuration using a reflection illumination system. In FIG. 2, the reflection illumination optical system 172 includes a lens 50, a lens 52 (e.g., tube lens), the beam splitter 174, and the objective lens 104. The image forming optical system 176 includes a lens 60 (e.g., tube lens), a collimating lens 62, and an image forming lens 64. Here, each lens may be configured by one lens or combination of a plurality of lenses. In the optical path of the reflection illumination optical system 172, a reticle 182 (first reticle) is arranged at the front side of a conjugate position 183 of the TDI sensor 105 facing the surface of the substrate 101, along the optical axis direction. Moreover, in the optical path of the reflection illumination optical system 172, a reticle 184 (second reticle) is arranged at the back side of the conjugate position 183 of the TDI sensor 105 facing the surface of the substrate 101, to be equivalently opposite to the reticle 182, along the optical axis direction.

A reflection inspection light irradiates the mask substrate 101 by the reflection illumination optical system 172. Referring to the case of FIG. 2, a specific example will be described. The reflection inspection light passes through the lens 50, and illuminates the reticle 182. Then, the light having passed through the reticle 182 illuminates the reticle 184. The light having passed through the reticle 184 passes through the lens 52 to be reflected by the beam splitter 174. The light reflected by the beam splitter 174 enters the objective lens 104, and forms an image on the pattern forming surface of the mask substrate 101 from the pattern forming surface side of the mask substrate 101 by the objective lens 104. Actually, the reticle image of the reticle 182 is formed at the front side of the pattern forming surface of the mask substrate 101, and the reticle image of the reticle 184 is formed at the back side of the pattern forming surface of the mask substrate 101. A catoptric light reflected from the mask substrate 101 passes through the objective lens 104 and the beam splitter 174. The light having passed through the beam splitter 174 enters the image forming optical system 176. In the image forming optical system 176, the light passes through the lens 60 and the collimating lens 62, and forms an image on the TDI sensor 105 by the image forming lens 64.

Figure 3:
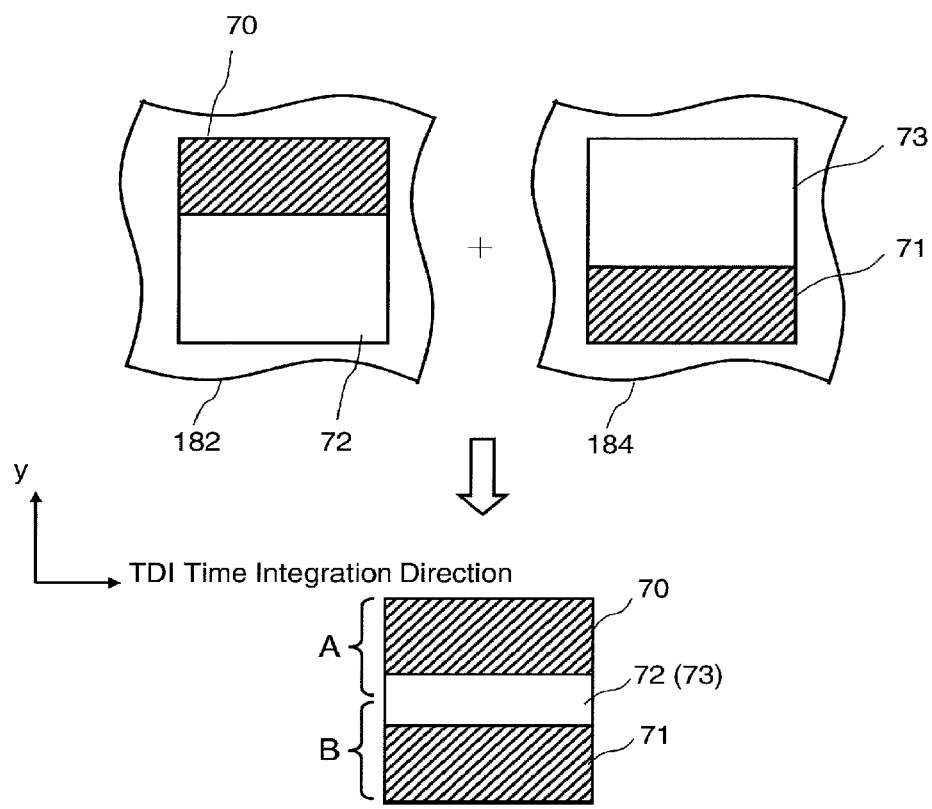
FIG. 3 shows examples of pattern configurations of reticles according to the first embodiment.

FIG. 3 shows examples of pattern configurations of reticles according to the first embodiment. In FIG. 3, a light-shielding pattern 70 whose end part is parallel with the direction of time integration of the TDI sensor 105, and a transmission pattern 72 whose occupancy rate in the illumination region is larger than that of the light-shielding pattern 70 are formed on the reticle 182. In the case of FIG. 3, the light-shielding pattern 70 occupies the upper part of the illumination region. The transmission pattern 72 occupies the region lower than the light-shielding pattern 70 in the illumination region. On the reticle 184, a light-shielding pattern 71 and a transmission pattern 73 are formed such that the direction relation between the light-shielding pattern and the transmission pattern is opposite to that of the reticle 182. In the case of FIG. 3, the light-shielding pattern 71 occupies the lower part of the illumination region. The transmission pattern 73 occupies the region upper than the light-shielding pattern 71 in the illumination region. Thus, the reticles 182 and 184 are arranged such that the directions of the patterns are opposite each other. Although, in the case of FIG. 3, the sizes of the light-shielding patterns 70 and 71 are mutually the same, and the sizes of the transmission patterns 72 and 73 are also mutually the same between the reticles 182 and 184, it is not limited thereto. The sizes do not need to be the same each other in the illumination region as long as the occupancy of the transmission pattern 72 is larger than that of the light-shielding pattern 70, and the occupancy of the transmission pattern 73 is larger than that of the light-shielding pattern 71. However, the end part, at the transmission pattern 72 side, of the light-shielding pattern 70, and the end part, at the transmission pattern 73 side, of the light-shielding pattern 71 should be straight lines in parallel with the direction of time integration of the TDI sensor 105.

Figure 4:
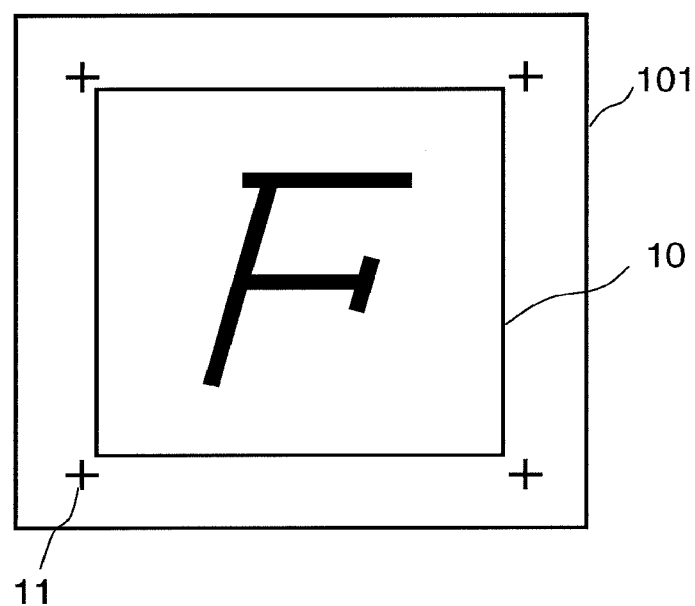
FIG. 4 shows a substrate structure according to the first embodiment.

FIG. 4 shows a substrate structure according to the first embodiment. In FIG. 4, a pattern (F) to be inspected is formed in an inspection region 10 of the substrate 101. For performing a pattern inspection of such a target object, first, it is necessary to adjust (align) a position of arrangement position including a rotational displacement of the substrate 101. For this purpose, on the substrate 101, a plurality of alignment marks 11 for alignment are formed around the inspection region 10 or in the inspection region 10. In the case of FIG. 4, a plurality of alignment marks 11 are formed in the vicinity of the outside of the four corners of the inspection region 10. Similarly to a pattern to be inspected, a plurality of alignment marks 11 are formed by light-shielding film patterns using, for example, a chromium (Cr) film or the like on, for example, a transparent quartz substrate. For performing alignment of the substrate 101, first, the positions of a plurality of alignment marks 11 need to be measured. Therefore, the position of each of a plurality of alignment marks 11 has to be measured in the visual field of the TDI sensor 105. However, even if it is intended to place the alignment mark 11 in the visual field of the TDI sensor 105, based on the position of the alignment mark 11 acquired from design information such as writing data, focus is not correct in the initial stage. Accordingly, it is difficult to identify the alignment mark 11 so highly accurately as to acquire the position of the alignment mark 11 based on a measured target image by the TDI sensor 105. Therefore, focusing should be performed between the position of the alignment mark 11 and the TDI sensor 105.

Figure 5A:
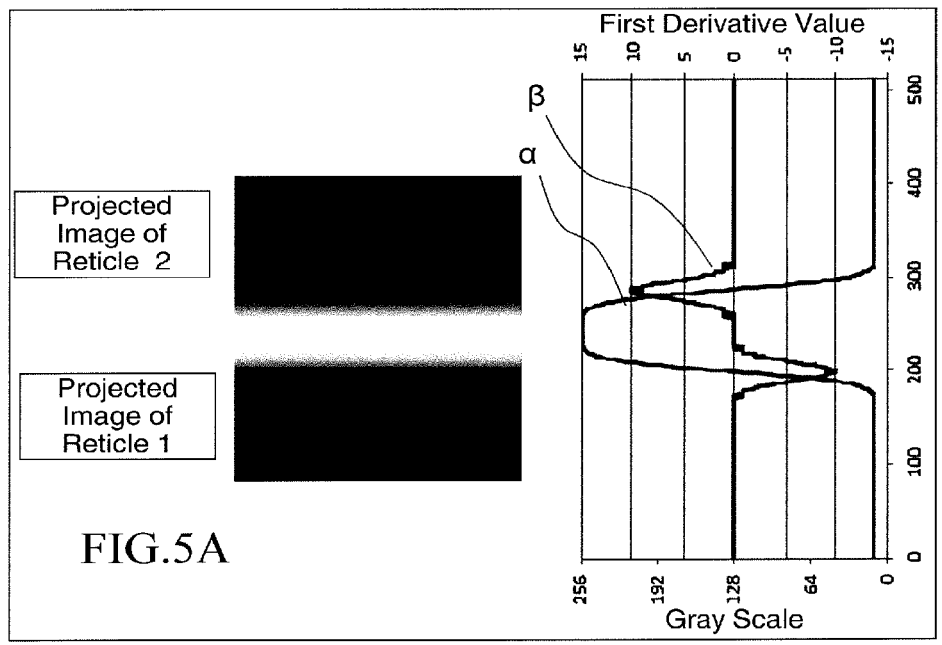
FIGS. 5A and 5B show examples of a measured target image according to the first embodiment and a comparative example.
Figure 5B:
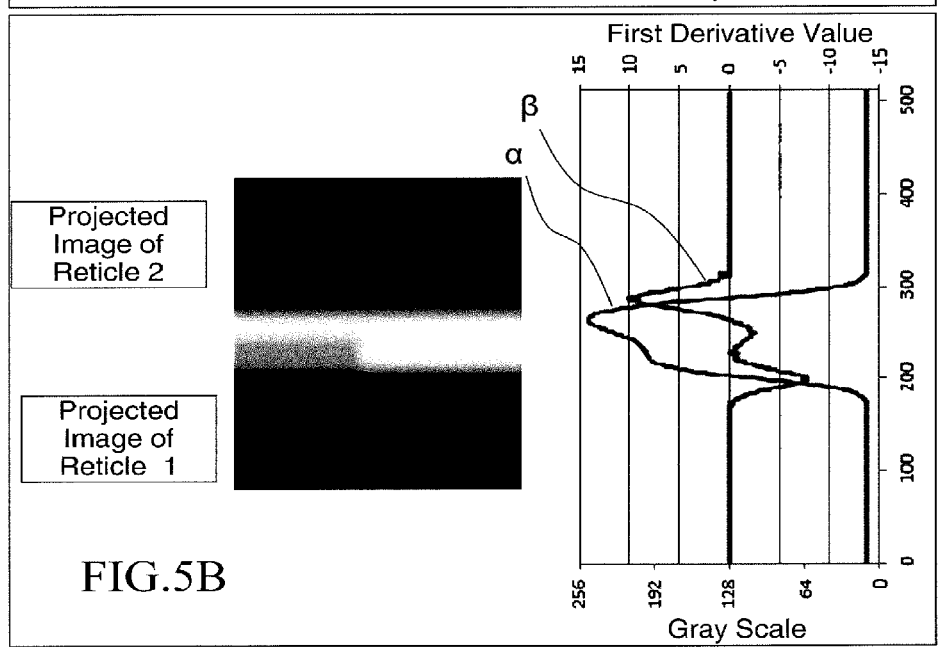
Figure 6:
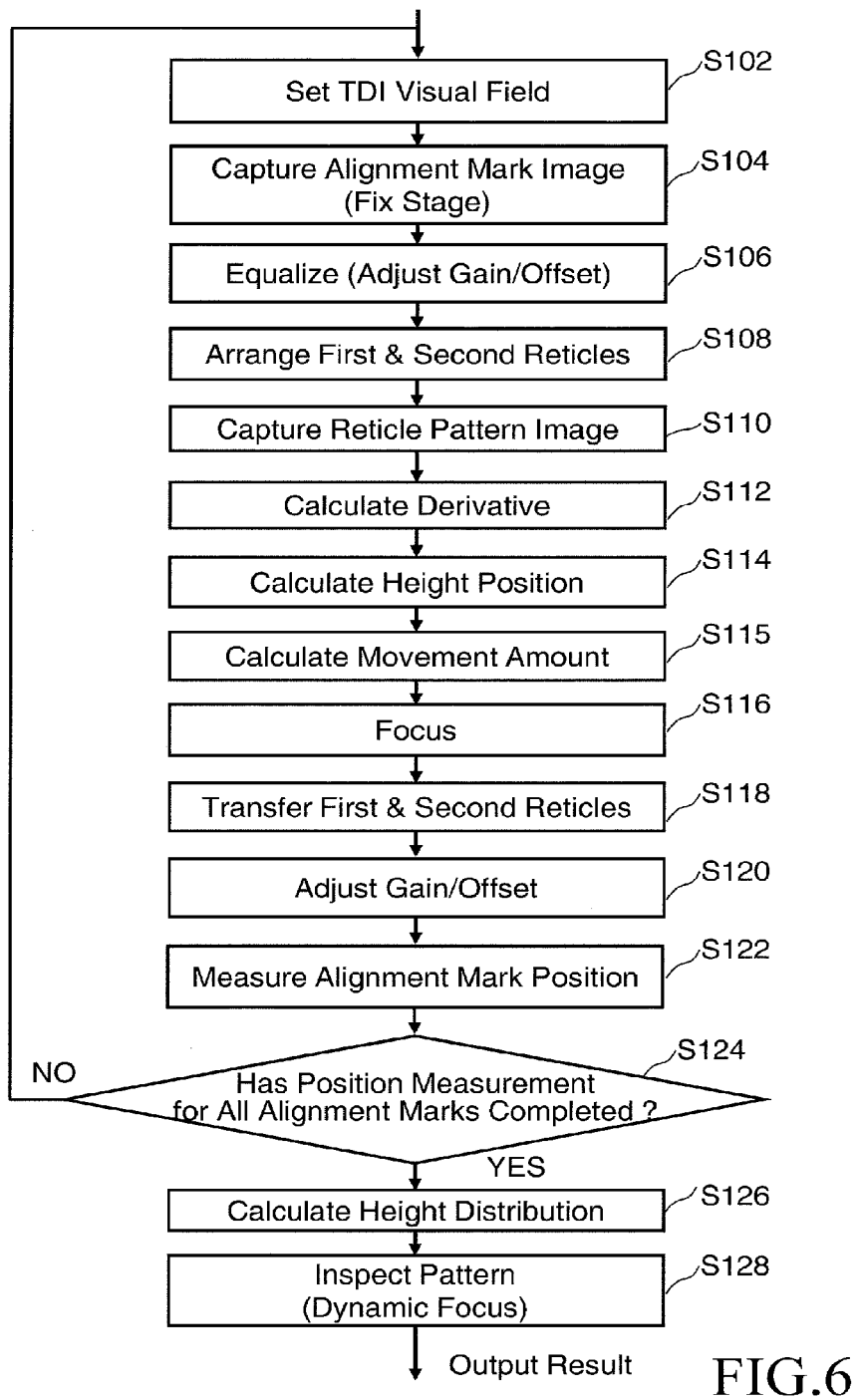
FIG. 6 is a flowchart showing main steps of a pattern inspection method according to the first embodiment.

FIGS. 5A and 5B show examples of a measured target image according to the first embodiment and a comparative example. A reticle image having passed through the reticles 182 and 184 irradiates the position of the alignment mark 11 of the substrate 101, and its reflected image is captured by the TDI sensor 105. In such a case, reflectance from the substrate 101 is not uniform because there exists the alignment mark 11. Therefore, in the comparative example, as shown in FIG. 5B, the pattern image of the alignment mark 11 is taken as background in the image. In such a state, the gray scale value of an acquired reticle image is in disorder. Although a focusing position is the position where a first derivative (differential) value of the gray scale value of the end part at the reticle 182 side of the light-shielding pattern 70 and a first derivative (differential) value of the gray scale value of the end part at the reticle 184 side of the light-shielding pattern 71 are symmetrical as shown in FIG. 5A, since the gray scale value of an acquired image is in disorder as shown in FIG. 5B, it is difficult to adjust a focus with high precision. Then, according to the first embodiment, this problem is solved by generating a state where such background image has been deleted. For achieving the solution, it operates as follows:

FIG. 6 is a flowchart showing main steps of a pattern inspection method according to the first embodiment. In FIG. 6, the pattern inspection method of the first embodiment executes a series of steps: a TDI visual field setting step (S102), an alignment mark imaging step (S104), an equalization step (S106), a reticle arrangement step (S108), a reticle pattern image capture step (S110), a derivative (differential) calculation step (S112), a height position calculation step (S114), a distance change/move amount calculation step (S115), a focusing step (S116), a reticle transfer step (S118), a gain/offset adjustment step (S120), an alignment mark position measuring step (S122), a determination step (S124), a height distribution calculation step (S126), and a pattern inspection step (S128).

Some of a plurality of steps described above are corresponding to a series of steps of a focusing method according to the first embodiment. Specifically, the following steps correspond to the focusing method of the first embodiment: the TDI visual field setting step (S102), the alignment mark imaging step (S104), the equalization step (S106), the reticle arrangement step (S108), the reticle pattern image capture step (S110), the derivative calculation step (S112), the height position calculation step (S114), the distance change/move amount calculation step (S115), the focusing step (S116), the reticle transfer step (S118), the gain/offset adjustment step (S120), the alignment mark position measuring step (S122), and the determination step (S124).

In the TDI visual field setting step (S102), the table control circuit 114 moves the XYθ table 102 to the position where one of a plurality of alignment marks 11 is irradiated with a reflection illumination light. The TDI sensor 105 is arranged at the position where a catoptric light of a reflection illumination light (illumination light for reflection) irradiating the substrate 101 can be received. In other words, the table control circuit 114 moves the XYθ table 102 to the position where one of a plurality of alignment marks 11 is in the visual field of the TDI sensor 105.

In the alignment mark imaging step (S104), in the state where the reticles 182 and 184 are out of the optical path, the optical image acquisition unit 150 irradiates the substrate 101 with a reflection illumination light, and acquires a reflected image from the substrate 101. Specifically, it operates as follows: First, as a precondition, the reticle control circuit 146 drives the reticle drive mechanism 185 to move the reticles 182 and 184 to the outside of the optical path. The reflection illumination optical system 172 illuminates the substrate 101, on which the pattern of the alignment mark 11 is formed, with a reflection illumination light not passing through the reticles 182 and 184.

Then, the TDI sensor 105 receives the pattern image of the alignment mark 11 of the substrate 101 through the image forming optical system 176 which forms a pattern image on the substrate 101. At this time, in the state where the substrate 101 is stopped, the TDI sensor 105 is made to receive the pattern image of the alignment mark 11 of the substrate 101. Specifically, while imaging the alignment mark 11, the table control circuit 114 keeps stopping the XYθ table 102.

Figure 7:
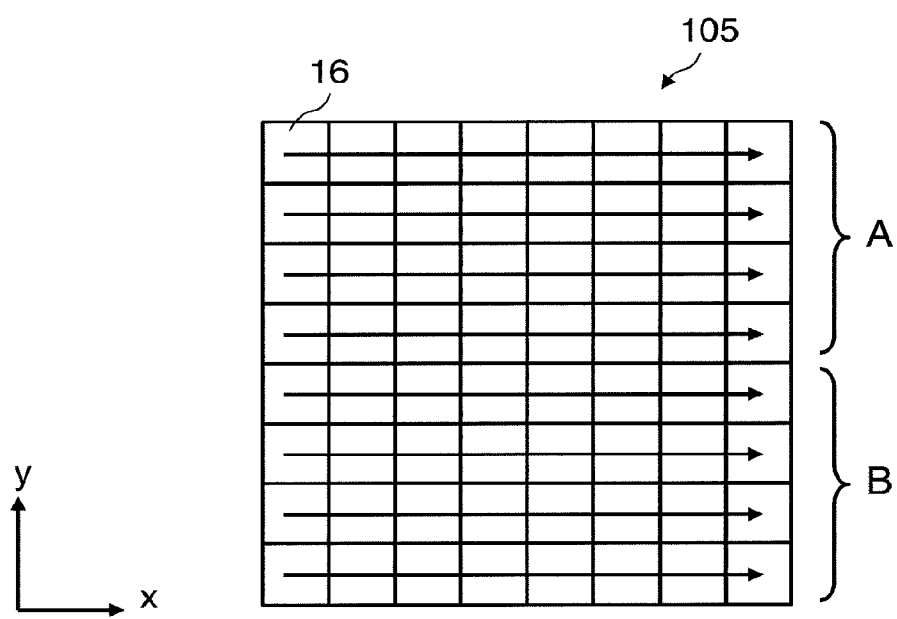
FIG. 7 shows an example of an image capturing method of a TDI sensor according to the first embodiment.

FIG. 7 shows an example of an image capturing method of a TDI sensor according to the first embodiment. As shown in FIG. 7, in the TDI sensor 105, a plurality of light receiving elements 16 (photo diodes) to be photoelectrically converted are arranged in a two-dimensional array. Then, an electric charge converted according to the light quantity of a light received by each light receiving element 16 is transmitted one by one at a predetermined timing to an adjacent light receiving element 16 in the direction (e.g., x direction) opposite to the imaging direction so as to be accumulated (integrated). Therefore, by moving the XYθ table 102, to be in synchronization with the charge transfer speed of the TDI sensor 105, in the time integration direction (electric charge movement direction) (opposite direction to imaging direction: e.g., x direction) of the TDI sensor 105, electric charges at the same position on the mask substrate 101 captured by different light receiving elements 16 are sequentially accumulated. Thus, each position on the mask substrate 101 is measured based on electric charges summed in the direction of time integration of the TDI sensor 105 (e.g., x direction).

Figure 8A:
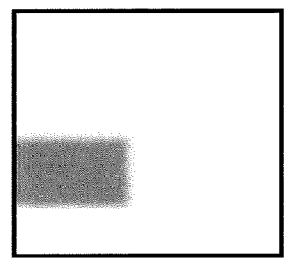
FIGS. 8A to 8D show examples of an image captured by a TDI sensor according to the first embodiment.
Figure 8B:
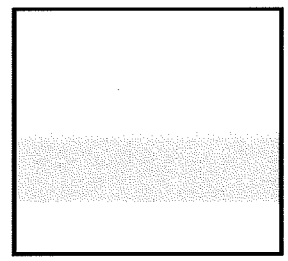

FIGS. 8A to 8D show examples of an image captured by a TDI sensor according to the first embodiment. As described in FIG. 7, if image capturing is performed while moving the XYθ table 102, to be in synchronization with the charge transfer speed of the TDI sensor 105, in the direction (e.g., x direction) of time integration of the TDI sensor 105, the pattern image of the alignment mark 11 is captured at the position not changed as shown in FIG. 8A. However, in this situation, since the focus is not adjusted, image capturing is performed in the out-of-focus state being blurred. Therefore, if this situation remains unchanged, the pattern image of the alignment mark 11 in such a blurred state will remain as a background. Therefore, according to the first embodiment, image capturing is intentionally performed without moving the XYθ table 102 in the direction (e.g., x direction) of time integration of the TDI sensor 105. Thereby, each electric charge accumulated by the row of the light receiving elements 16 arrayed in the direction (e.g., x direction) of time integration of the TDI sensor 105 is equivalent to an electric charge acquired at a position different from each other on the substrate 101. Consequently, the acquired image can be an image averaged in the direction of time integration of the TDI sensor 105 as shown in FIG. 8B. As described above, gray scale data is generated by receiving a pattern image (pattern image of the alignment mark 11) of the substrate 101 by the TDI sensor 105 in the state where the substrate 101 is stopped.

In the equalization step (S106), the gain/offset adjustment circuit 140 (equalizing unit or "equalizing circuit") performs gray scale value equalization by using a gray scale value output by the TDI sensor 105 which received a pattern image (pattern image of the alignment mark 11) of the substrate 101 generated by irradiating the substrate 101 with a reflection illumination light not passing though the reticles 182 and 184.

Figure 8C:
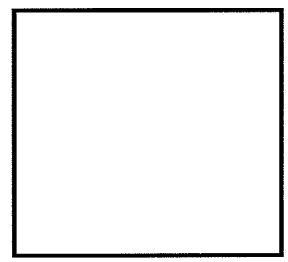

Specifically, it operates as follows: Measured target data (gray scale data) output by the TDI sensor 105 is input into the sensor circuit 106. The sensor circuit 106 performs A/D (analog to digital) conversion of the input measured target data in order to generate gray scale value data. Then, the generated gray scale value data is stored in the stripe pattern memory 123 to be output to the gain/offset adjustment circuit 140 and displayed on the pattern monitor 118. On this occasion, the gain/offset adjustment circuit 140 controls setting of gain/offset of the sensor circuit 106. Specifically, the gain/offset adjustment circuit 140 performs gray scale value equalization as shown in FIG. 8C by adjusting gain/offset of a gray scale value output by the TDI sensor 105 by using gray scale data averaged in the direction of time integration of the TDI sensor 105. In other words, equalization is performed so that blurred halftone patterns may be unidentifiable. Thereby, the pattern image of the alignment mark 11 being a background can be erased.

At the present stage, it is unknown what has been imaged as a pattern image of the substrate 101. Therefore, if equalizing is performed without averaging, there is a possibility that the amount of adjustment of gain and offset is increased. On the other hand, according to the first embodiment, the adjustment amount of gain and offset can be reduced by equalizing the gray scale value of the image averaged in the direction of time integration of the TDI sensor 105. Therefore, it is possible to avoid a risk that identification of a reticle image becomes difficult because of equalization without averaging as to be described later.

In the reticle arrangement step (S108), the reticle control circuit 146 drives the reticle drive mechanism 185 to transfer the reticles 182 and 184 to be in the optical path. Specifically, the reticle drive mechanism 185 arranges the reticle 182, along the optical axis direction, at the front side of the conjugate position of the TDI sensor 105 facing the surface of the substrate 101 in the optical path of the reflection illumination optical system 172. Moreover, the reticle drive mechanism 185 arranges the reticle 184, along the optical axis direction, at the back side of the conjugate position of the TDI sensor 105 facing the surface of the substrate 101 in the optical path of the reflection illumination optical system 172, to be equivalently opposite to the reticle 182 such that patterns of the reticles 182 and 184 have opposite directions from each other.

In the reticle pattern image capture step (S110), in the state where equalization has been performed in the equalization step (S106), the optical image acquisition unit 150 irradiates the substrate 101 with a reflection illumination light having passed through the reticles 182 and 184, and acquires a reflected image from the substrate 101. Specifically, it operates as follows: The reflection illumination optical system 172 illuminates the substrate 101, on which the pattern of the alignment mark 11 has been formed, with a reflection illumination light (reticle image) having passed through the reticles 182 and 184. In the illumination region of the reflection illumination light illuminating the reticle 182, the light-shielding pattern 70 occupies, for example, all the upper part of the illumination region. Therefore, the reflection illumination light can pass through only the region of the transmission pattern 72. Since a pattern similar to that of the reticle 182 is formed on the reticle 184 by vertically reversing the pattern of the reticle 182, all the lower part of the illumination region illuminated with a reflection illumination light illuminating the reticle 184 is occupied with the light-shielding pattern 71. Therefore, the reflection illumination light can pass through only the region where the transmission patterns 72 and 73 overlap with each other.

In the state where equalization has been performed, the TDI sensor 105 receives, through the image forming optical system 176, a pattern image (reticle image) of the substrate 101 generated by illuminating the substrate 101 with a reflection illumination light (reticle image) having passed through the reticles 182 and 184. Measured target data (gray scale data) output by the TDI sensor 105 is input into the sensor circuit 106. The sensor circuit 106 performs A/D (analog to digital) conversion of the input measured target data in order to generate gray scale value data. The gray scale value is defined by 256 gray scales from 0 to 255, for example.

Figure 8D:
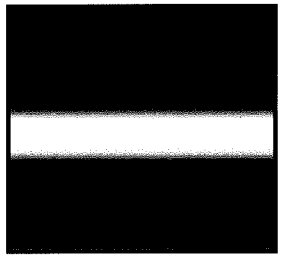

Here, when performing image capturing by the TDI sensor 105, the TDI sensor 105 receives a reticle image from the substrate 101 in the state where the substrate 101 is stopped. Specifically, while capturing the image of the alignment mark 11, the table control circuit 114 keeps stopping the XYθ table 102. According to the first embodiment, image capturing is intentionally performed without moving the XYθ table 102 in the direction (e.g., x direction) of time integration of the TDI sensor 105. Thereby, each electric charge accumulated by the row of the light receiving elements 16 arrayed in the direction (e.g., x direction) of time integration of the TDI sensor 105 is equivalent to an electric charge acquired at a position different from each other on the substrate 101. Consequently, the acquired image can be an image in which no background pattern is taken, and which has been averaged in the direction of time integration of the TDI sensor 105 as shown in FIG. 8D. As described above, each of the end parts of the light-shielding patterns 70 and 71 (end parts of the transmission patterns 72 and 73) of the reticles 182 and 184 is formed in parallel with the direction of time integration. In other words, the reticle pattern has been formed to be a pattern of the shape which does not change depending on the direction of time integration of the TDI sensor 105 (e.g., x direction). This reticle pattern is imaged by the TDI sensor 105. In such a case, the row of the light receiving elements 16 arrayed in the x direction continue to capture images on the same line pattern. As a result, as shown in FIG. 8D, the reticle pattern image extending in the x direction (time axis) can be acquired. Since each of the end parts (end parts of the transmission patterns 72 and 73) of the light-shielding patterns 70 and 71 is formed in parallel with the direction of time integration, even if the image is averaged, there is no mixture of monochrome patterns. Therefore, the gray scale value of the captured image can be as high level as the gray scale value of the image obtained when performing image capturing while moving the XYθ table 102 to be in synchronization with the charge transfer speed of the TDI sensor 105. Accordingly, the reticle pattern can be identified even if image capturing is performed in the state where gain/offset adjustment has been performed sufficiently enough to erase the background (alignment mark 11) whose gray scale value was decreased by averaging. Moreover, by identifying a focusing position by using a reticle pattern image averaged in the direction of time integration of the TDI sensor 105 as to be described later, it becomes possible to focus on the position averaged in the visual field of the TDI sensor 105, thereby averaging errors with respect to a height position.

Measured target data (gray scale data) output by the sensor circuit 106 is stored in the stripe pattern memory 123 to be output to the height distribution generation circuit 142 and displayed on the pattern monitor 118.

Figure 9:
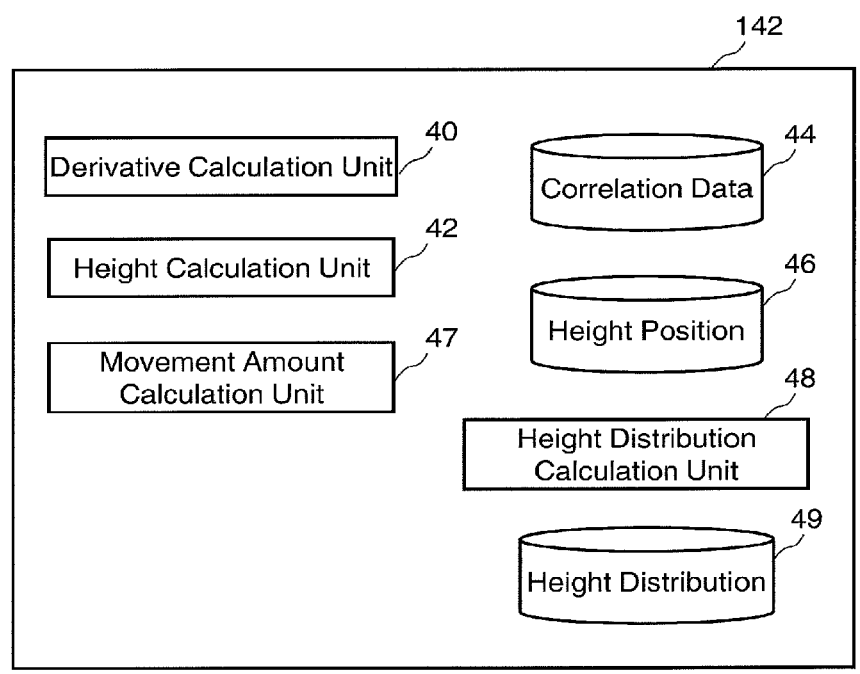
FIG. 9 shows an example of an internal structure of a height distribution generation circuit according to the first embodiment.

FIG. 9 shows an example of the internal structure of a height distribution generation circuit according to the first embodiment. As shown in FIG. 9, in the height distribution generation circuit 142, there are arranged a derivative (differential) calculation unit 40, a height calculation unit 42, a distance change/move amount calculation unit 47, a height distribution calculation unit 48, and storage devices 44, 46, and 49, such as magnetic disk devices. Each of the "units" such as the derivative calculation unit 40, the height calculation unit 42, the distance change/move amount calculation unit 47, and the height distribution calculation unit 48 includes a processing circuitry. As the processing circuitry, for example, an electric circuit, computer, processor, circuit board, quantum circuit, or semiconductor device may be used. Each of the "units" may use a common processing circuitry (same processing circuitry), or different processing circuitries (separate processing circuitries). Input data required in the derivative calculation unit 40, the height calculation unit 42, the distance change/move amount calculation unit 47, and the height distribution calculation unit 48, and calculated results are stored in a memory (not shown) each time.

In the derivative (differential) calculation step (S112), in the state where equalization has been performed, the derivative calculation unit 40 calculates a first derivative (differential) value of a gray scale by using a gray scale value output by the TDI sensor 105 which received a reticle pattern image (pattern image) of the substrate 101 generated by irradiating the substrate 101 with a reflection illumination light having passed through the reticles 182 and 184.

FIGS. 10A to 10D show examples of a relation between a first derivative value of a gray scale value and a focus position according to the first embodiment. As described above, the reticle 182 is arranged at the front side of the conjugate position of the TDI sensor 105. Therefore, the reticle image of the reticle 182 is focused (formed) at the front side (lower position in the height-wise direction (z direction)) of the pattern forming surface of the substrate 101, along the direction of the optical axis direction. In other words, when the substrate 101 is moved to the position (−z direction) lower than the focusing height position formed (focused) at the conjugate position of the TDI sensor 105, along the height-wise direction (z direction), and arranged at a focusing position z1 of the reticle image of the reticle 182, an absolute value A of the first derivative value of the gray scale of the image at the pattern end part at the reticle 182 side becomes maximum as shown in FIG. 10R. Conversely, an absolute value B of the first derivative value of the gray scale of the image at the pattern end part at the reticle 184 side becomes minimum. Meanwhile, the reticle 184 is arranged at the back side of the conjugate position of the TDI sensor 105. Therefore, the reticle image of the reticle 184 is formed (focused) at the back side (higher position in the height-wise direction (z direction)) of the pattern forming surface of the substrate 101, along the direction of the optical axis. In other words, when the substrate 101 is moved to the position (+z direction) higher than the focusing height position formed (focused) at the conjugate position of the TDI sensor 105, along the height-wise direction (z direction), and arranged at a focusing position z2 of the reticle image of the reticle 184, the absolute value B of the first derivative value of the gray scale of the image at the pattern end part at the reticle 184 side becomes maximum as shown in FIG. 10C. Conversely, the absolute value A of the first derivative value of the gray scale of the image at the pattern end part at the reticle 182 side becomes minimum. When the substrate 101 is arranged at a focusing height position z0 formed (focused) at the conjugate position of the TDI sensor 105, the absolute values A and B of the first derivative values of the gray scales of the images at the pattern end parts at the sides of the reticles 182 and 184 are the same as each other as shown in FIG. 10B.

Then, there are measured in advance by experiment, etc. the absolute value A of the first derivative value of the gray scale of the pattern end part at the reticle 182 side, and the absolute value B of the first derivative value of the gray scale of the pattern end part at the reticle 184 side, in the case where the height position z (height position of the XYθ table 102) of the pattern forming surface of the substrate 101 are set to be variable. Next, a subtracted value (A−B) is obtained by subtracting the absolute value B of the first derivative value of the gray scale of the pattern end part at the reticle 184 side from the absolute value A of the first derivative value of the gray scale of the pattern end part at the reticle 182 side. Moreover, an added value (A+B) is obtained by adding the absolute value A of the first derivative value and the absolute value B of the first derivative value. Then, a correlation is obtained between a value "f" calculated by dividing the subtracted value (A-B) by the added value (A+B), and a height position z (height position of the XYθ table 102) of the pattern forming surface of the substrate 101. "f" can be defined by the following equation (1).

$$f=(A-B)/(A+B) \quad (1)$$

When acquiring data of such a correlation, a quartz substrate, on which no pattern has been formed yet, being a base of the substrate 101 may be used. At that time, it is sufficient to perform gain/offset adjustment on the assumption of the level around the same as the equalization processing described above. In FIG. 10D, the ordinate axis represents a value "f" calculated by dividing the subtracted value (A−B), which is obtained by subtracting the absolute value B of the first derivative value at the reticle 184 side from the absolute value A of the first derivative value at the reticle 182 side, by the added value (A+B), which is obtained by adding the absolute value A of the first derivative value and the absolute value B of the first derivative value. The abscissa axis represents a height position z of the pattern forming surface of the substrate 101. When the height position z of the pattern forming surface of the substrate 101 is a focusing position z0 formed (focused) at the conjugate position of the TDI sensor 105, f=0. Here, as shown in FIG. 10D, "f" is in a linear proportion at the positions front and back of the focusing position z0. Therefore, by using such relation, it is possible to obtain the height position z of the pattern forming surface of the substrate 101 at the time of actual measurement. The height position z of the pattern forming surface of the substrate 101 can be defined by the following equation (2). k is a coefficient of the correlation equation.

$$z'=k\cdot f=k\cdot (A-B)/(A+B) \quad (2)$$

The correlation data (coefficient k of a correlation equation) is input from the outside of the inspection apparatus 100, and stored in the storage device 44.

In the height position calculation step (S114), the height calculation unit 42 measures a height position z' of the substrate 101 by using a first derivative value of the gray scale value output by the TDI sensor 195 which received an alignment pattern image of the substrate 101 generated by illuminating the substrate 101 with a reflection illumination light having passed through the reticles 182 and 184, in the gain and offset adjustment state where equalization has been performed. Specifically, the height calculation unit 42 reads correlation data (coefficient k of a correlation equation) from the storage device 44, and calculates a height position z' of the pattern forming surface of the substrate 101 by using the equation (2).

In the distance change/move amount calculation step (S115), the distance change/move amount calculation unit 47 calculates a distance change/move amount Δz of a relative distance between the substrate 101 and the conjugate position of the TDI sensor, for focusing the reticle pattern image (pattern image) of the substrate 101. The distance change/move amount calculation unit 47 calculates a distance change/move amount Δz of a relative distance, for focusing the pattern image of the substrate 101, between the substrate 101 and the conjugate position of the TDI sensor by using a first derivative value of the gray scale value output by the TDI sensor 105 which received a pattern image of the substrate 101 generated by illuminating the substrate 101 with a reflection illumination light having passed through the reticles 182 and 184 in the state where equalization has been performed. Specifically, the distance change/move amount Δz can be obtained by calculating a difference by subtracting a height position z' acquired by measurement from a focusing height position z0 where the pattern forming surface of the substrate 101 is focused on the conjugate position of the TDI sensor 105.

In the focusing step (S116), under the control of the focus circuit 144, the drive mechanism 186 (drive unit) changes the relative distance between the substrate 101 and the conjugate position of the TDI sensor 195 by using the distance change/move amount Δz. Specifically, the drive mechanism 186 (drive unit) moves the XYθ table 102 in the height-wise direction (z direction) by the distance change/move amount Δz. Thereby, it becomes possible to focus the reticle image at the capturing position.

Although, in the example described above, focusing is performed using a value calculated by dividing a subtracted value of two absolute values of first derivative values of gray scale by an added value of the two absolute values of the first derivative values of gray scale, it is not limited thereto. By first differentiating acquired gray scale value data, the data of the first derivative value shown in the graph p of FIG. 5A is acquired. Then, the relative distance between the substrate 101 and the conjugate position of the TDI sensor 195 may be changed/moved to the position where the graph of the first derivative value of the end part of the light-shielding pattern 70 on the reticle 182 and the graph of the first derivative value of the end part of the light-shielding pattern 71 on the reticle 184 are symmetrical. Thereby, it becomes possible to focus the reticle image at the capturing position. The height position z' of the image capturing position of the reticle image can be calculated from the distance change/move amount Δz based on a moved distance.

In the reticle transfer step (S118), the reticle control circuit 146 drives the reticle drive mechanism 185 to transfer the reticles 182 and 184 on the optical path to the outside of the optical path.

In the gain/offset adjustment step (S120), the gain/offset adjustment circuit 140 performs controlling so as to change the setting of gain and offset of the sensor circuit 106 so that a pattern image of the alignment mark 11 output by the TDI sensor 105 may be identified.

In the alignment mark position measuring step (S122), the optical image acquisition unit 150, first, irradiates the substrate 101 with a reflection illumination light and acquires a reflected image from the substrate 101, in the state where the reticles 182 and 184 are out of the optical path. Specifically, it operates as follows: The reflection illumination optical system 172 illuminates the substrate 101, on which the pattern of the alignment mark 11 is formed, with a reflection illumination light not having passed through the reticles 182 and 184.

Then, the TDI sensor 105 receives the pattern image of the alignment mark 11 of the substrate 101 through the image forming optical system 176 which forms a pattern image of the substrate 101. At this time, image capturing is performed while moving the XYθ table 102, to be in synchronization with the charge transfer speed of the TDI sensor 105, in the direction of time integration of the TDI sensor 105. That is, the image capturing is performed using the TDI sensor 105 based on its original usage method. Measured target data (gray scale data) output by the TDI sensor 105 is input into the sensor circuit 106. The sensor circuit 106 performs A/D (analog to digital) conversion of the input measured target data in order to generate gray scale value data. The gray scale value is defined by 256 gray scales from 0 to 255, for example. The measured target data (gray scale data) output by the sensor circuit 106 is stored in the stripe pattern memory 123 to be output to the control system circuit 160 and displayed on the pattern monitor 118. Since the focus position has already been adjusted to be in focus, the alignment mark 11 can be clearly identified based on the image acquired. Therefore, the position of the XYθ table 102 is adjusted so that the center of the alignment mark 11 may be in the visual field of the TDI sensor 105 in order to measure the center position (x, y) of the alignment mark 11. In connection with the center position (x, y) of the alignment mark 11, information on a calculated height position z' at that position is stored in the storage device 46.

In the determination step (S124), the control computer 110 determines whether position measurement for all the alignment marks 11 has been completed. If there is an alignment mark 11 whose position has not been measured yet, it returns to the TDI visual field setting step (S102). Then, each step from the TDI visual field setting step (S102) to the determination step (S124) is repeated until position measurement for all the alignment marks 11 has been completed.

Thus, height positions z' at the positions of all the alignment marks 11 have been stored in the storage device 46.

In the height distribution calculation step (S126), the height distribution calculation unit 48 acquires a height position distribution of the substrate 101 by performing calculation using each height position of the substrate 101. Specifically, height at each position on the surface (inspection region 10) of the substrate 101 is calculated using a height position z' at the position of each alignment mark 11 of the substrate 101. The height at each position on the surface (inspection region 10) of the substrate 101 can be calculated by performing linear interpolation of height positions z' at the positions of four alignment marks 11. Distribution of calculated height positions of the substrate 101 is stored in the storage device 49.

Figure 11:
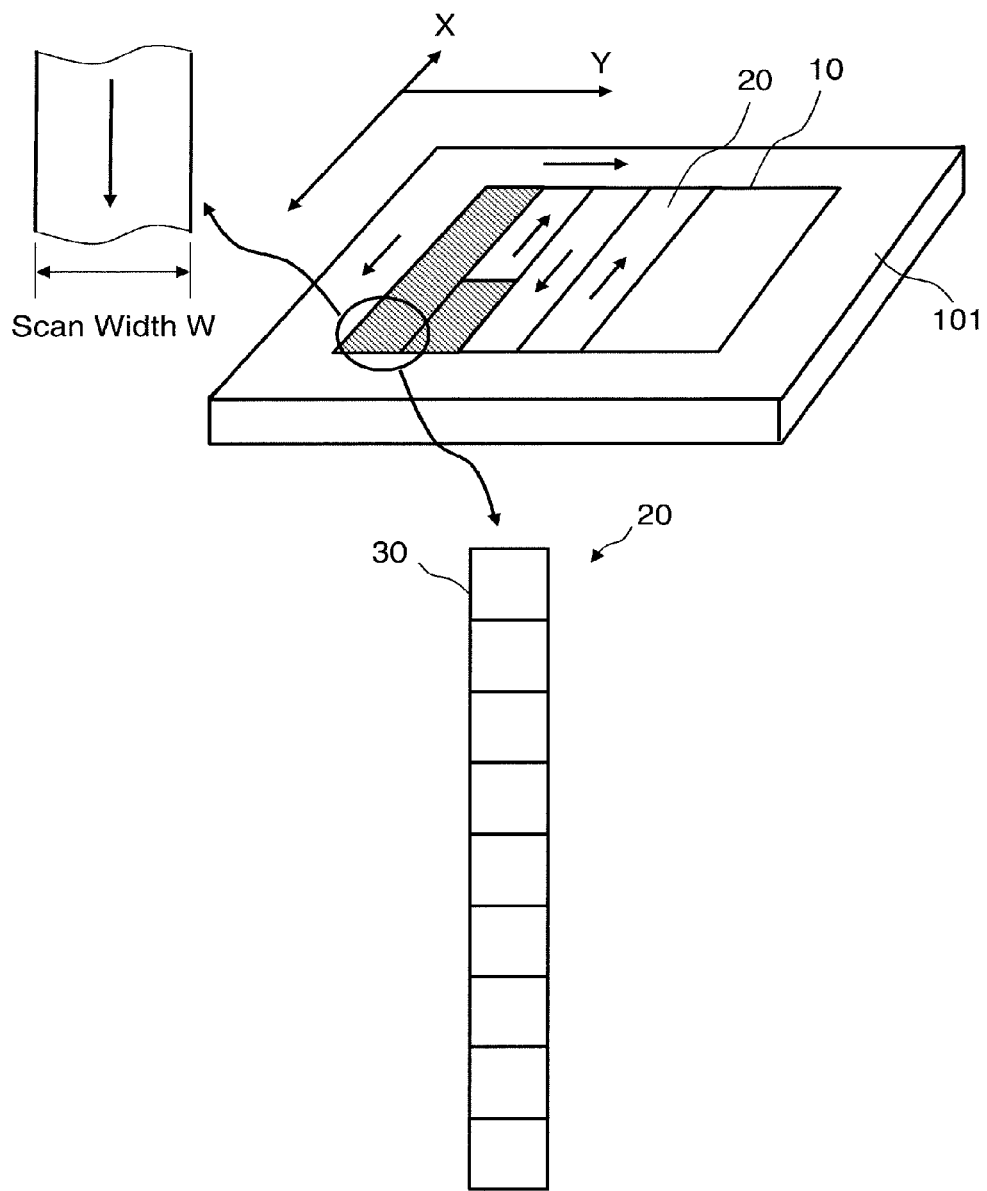
FIG. 11 is a conceptual diagram illustrating an inspection region according to the first embodiment.

In the pattern inspection step (S128), the optical image acquisition unit 150 acquires an optical image of a circuit pattern formed on the substrate 101 while changing the height position of the substrate 101, based on the height position distribution. Then, using the acquired optical image, inspection is performed to know whether a pattern defect exists or not. Specifically, it operates as follows:

FIG. 11 is a conceptual diagram illustrating an inspection region according to the first embodiment. As shown in FIG. 11, an inspection region 10 (entire inspection region) of the substrate 101 is virtually divided into a plurality of strip-shaped inspection stripes 20 each having a scan width W in the y direction, for example.

The inspection apparatus 100 acquires an image (stripe region image) from each inspection stripe 20. That is, with respect to each of the inspection stripes 20, the inspection apparatus 100 captures an image of a figure pattern arranged in the stripe region concerned by using a laser light in the longitudinal direction (x direction) of the stripe region concerned. Then, the XYθ table 120 is moved in the x direction, and accordingly, the TDI sensor 105, which continuously moves relatively in the x direction by the movement of the XYθ table 120, acquires an optical image at the position irradiated with the laser light. The TDI sensor 105 continuously captures optical images each having a scan width W as shown in FIG. 11. In other words, while moving relatively to the XYθ table 102 which moves in synchronization with the charge transfer speed of the TDI sensor 105, the TDI sensor 105 captures optical images of patterns formed on the substrate 101 by using an inspection light. As the inspection light, a light emitted from the transmission illumination system 170 may be used, or a light emitted from the reflection illumination optical system 172 may be used. When the reflection illumination optical system 172 emits a reflection illumination light, needless to say, the reticles 182 and 184 are transferred to be out of the optical path. According to the first embodiment, after capturing an optical image in one inspection stripe 20, the TDI sensor 105 moves in the y direction to the position of the next inspection stripe 20 and similarly captures another optical image having a scan width W continuously while moving in the direction reverse to the last image capturing direction. Thereby, the image capturing is repeated in the forward (FWD) and backward (BWD) directions, namely changing the direction reversely when advancing and returning.

The direction of the image capturing is not limited to repeating the forward (FWD) and backward (BWD) movement. Images may be captured in a fixed one direction. For example, it is sufficient to repeat FWD and FWD, or alternatively, to repeat BWD and BWD.

During the image capturing by the TDI sensor 105, under the control of the focus circuit 144, the drive mechanism 186 (drive unit) reads data of height position distribution from the storage device 49, acquires a height position z corresponding to the image capturing position, and moves the height position of the XYθ table 102 based on the distance change/move amount Δz being a difference from a focusing position z0. Thereby, focusing at an image capturing position can be dynamically adjusted.

The pattern image focused/formed on the TDI sensor 105 is photoelectrically converted by each light receiving element of the TDI sensor 105, and further analog-to-digital (A/D) converted by the sensor circuit 106. Then, pixel data for an inspection stripe 20 to be measured is stored in the stripe pattern memory 123. When image capturing the pixel data (stripe region image), a dynamic range where the maximum gray level is 60% incidence of the illumination light quantity, for example, is used as the dynamic range of the TDI sensor 105. When acquiring an optical image of the inspection stripe 20, the laser length measuring system 122 measures the position of the XYθ table 102. The measured position information is output to the position circuit 107. The position circuit 107 calculates the position of the mask substrate 101 by using the measured position information.

Then, the stripe region image is sent to the comparison circuit 108, with data indicating the position of the substrate 101 on the XYθ table 102 output from the position circuit 107. Measured target data (pixel data) is, for example, 8-bit unsigned data (256 gray scales), and indicates a gray level (light intensity) of brightness of each pixel.

In the reference image generation step, first, the development circuit 111 (an example of reference image generation unit) generates a design image by performing image development based on design pattern data being a basis for forming patterns of the mask substrate 101. Specifically, the development circuit 111 reads design data from the magnetic disk device 109 through the control computer 110, and converts (image development) each figure pattern in a target frame 30 defined in the read design data into image data of binary or multiple values so as to generate a design image.

Here, basics of figures defined by design pattern data are, for example, rectangles and triangles. For example, there is stored figure data (vector data) defining the shape, size, position, and the like of each pattern figure by using information, such as coordinates (x, y) of the reference position of the figure, lengths of sides of the figure, and a figure code serving as an identifier for identifying the figure type such as a rectangle, a triangle and the like.

When information of design pattern, used as figure data, is input to the development circuit 111, the data is developed into data of each figure. Then, figure codes, figure dimensions and the like indicating figure shapes in the data of each figure are interpreted. Then, the development circuit 111 develops design image data of binary or multiple values as patterns to be arranged in mesh regions in units of grids of predetermined quantization dimensions, and outputs the developed data. In other words, the development circuit 111 reads design data, calculates an occupancy rate occupied by a figure in the design pattern, for each mesh region obtained by virtually dividing an inspection region into squares in units of predetermined dimensions, and outputs n-bit occupancy rate data. For example, it is preferable that one mesh region is set as one pixel. Assuming that one pixel has a resolution of $1/2^8 (=1/256)$, the occupancy rate in each pixel is calculated by allocating small regions which corresponds to the region of the figures arranged in the pixel concerned and each of which is corresponding to a 1/256 resolution. Then, a design image of 8-bit occupancy rate data is generated for each pixel. Data of the design image is output to the reference circuit 112.

The reference circuit 112 (example of reference image generation unit) performs filtering processing of the design image to generate a reference image.

Figure 12:
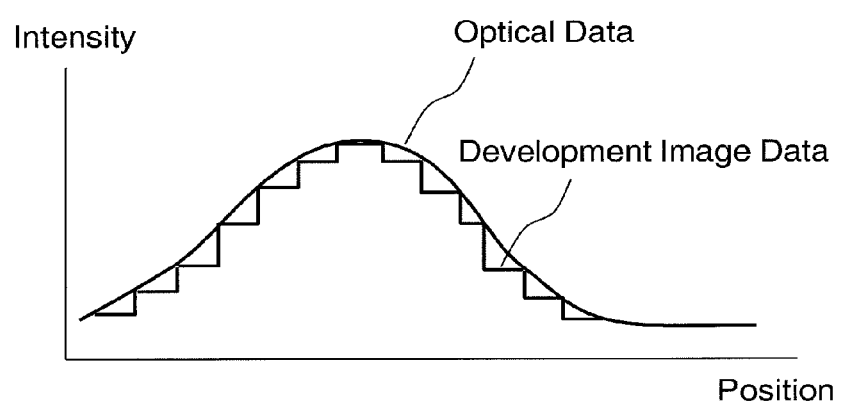
FIG. 12 illustrates filter processing according to the first embodiment.

FIG. 12 illustrates filter processing according to the first embodiment. Since measured target data being an optical image obtained from the sensor circuit 106 is in the state affected by the filtering due to resolution characteristics of the objective lens 104, an aperture effect of the TDI sensor 105, or the like, in other words, in the analog state continuously changing, it is possible to match reference design image data with the measured target data by also performing filter processing on the reference design image data being image data on the design side having image intensity (gray value) represented by digital values. In this manner, a reference image to be compared with a frame image (optical image) is generated. The generated reference image is output to the comparison circuit 108. Thus, data of image (reference image) being the other side to be compared for inspection is generated.

The stripe region image input into the comparison circuit 108 is stored in the storage device (not shown). The comparison circuit 108 divides the stripe region image by a predetermined size (e.g., the same width as the scan width W) in the x direction such that the frame image of a target frame region 30 is clipped from the stripe region image (optical image) of the inspection stripe 20. For example, it is divided into frame images each having 512×512 pixels. By this processing, a plurality of frame images (optical images) corresponding to a plurality of frame regions 30 are acquired. The size of the frame region 30 does not necessarily need to be the same width as the scanning width W. For example, it is preferable for the size of the frame region 30 to be 1/n (n is a natural number, and, for example, n=1 or 2) of the scanning width W.

With respect to a frame image (optical image) and a reference image which are to be compared, the comparison circuit 108 performs position alignment by using a predetermined algorithm. For example, the position alignment is performed using a least-squares method. The comparison circuit 108 compares the frame image (pattern image) with the reference image which have been aligned. Here, both the images are compared for each pixel according to a predetermined determination condition, and it is determined whether there is a defect, such as a shape defect. For example, according to a predetermined algorithm which is an example of the determination condition, both the images are compared for each pixel in order to determine whether a defect exists or not. For example, it is determined whether a difference value between the pixel values of both the images is larger than a determination threshold, and if the difference value is larger, it is determined there is a defect. Then, the comparison result may be output to the magnetic disk device 109, magnetic tape device 115, flexible disk device (FD) 116, CRT 117, and pattern monitor 118, or output from the printer 119.

As described above, according to the first embodiment, focusing can be performed highly accurately irrespective of patterns formed on the inspection substrate surface where a reticle image is projected. Thus, pattern inspection can be performed with high precision.

In the above description, each " . . . circuit" includes a processing circuitry. As the processing circuitry, for example, an electric circuit, computer, processor, circuit board, quantum circuit, semiconductor device, or the like can be used. Each " . . . circuit" may use a common processing circuitry (same processing circuitry), or different processing circuitries (separate processing circuitries). In the case of using programs, the programs are stored in a recording medium, such as a magnetic disk device, magnetic tape device, FD, ROM (Read Only Memory), etc. For example, each of the position circuit 107, the comparison circuit 108, the development circuit 111, the reference circuit 112, the autoloader control circuit 113, the table control circuit 114, and the like includes a processing circuit. As the processing circuitry, for example, an electric circuit, computer, processor, circuit board, quantum circuit, semiconductor device, or the like can be used.

Embodiments have been explained referring to concrete examples described above. However, the present invention is not limited to these specific examples. In the above examples, when capturing a background image, the image capturing is performed in the state where the XYθ table 102 is stopped in order to perform averaging by using the characteristics of the TDI sensor 105, but it is not limited thereto. It is also preferable, after performing image capturing while moving the XYθ table 102 in synchronization with the charge transfer speed of the TDI sensor 105, to average gray scale values of pixels arrayed in the time integration direction of an acquired image and then to use the acquired average value instead of the background image described above.

While the apparatus configuration, control method, and the like not directly necessary for explaining the present invention are not described, some or all of them can be selectively used on a case-by-case basis when needed. For example, although description of the configuration of the control circuit for controlling the inspection apparatus 100 is omitted, it should be understood that some or all of the configuration of the control circuit can be selected and used appropriately when necessary.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A focusing apparatus comprising:
   a reflection illumination optical system configured to illuminate a substrate, on which a pattern is formed, with a reflection illumination light;
   an image forming optical system configured to form a pattern image of the substrate;
   a time delay integration sensor (TDI sensor) configured to receive the pattern image of the substrate;
   a first reticle, arranged at a front side of a conjugate position of the TDI sensor facing a surface of the substrate, along an optical axis direction, in an optical path of the reflection illumination optical system, configured to be irradiated with the reflection illumination light, and have thereon a light-shielding pattern whose end part is parallel with a direction of time integration of the TDI sensor, and a transmission pattern whose occupancy rate in an illumination region is larger than that of the light-shielding pattern;
   a second reticle, arranged at a back side of the conjugate position of the TDI sensor facing the surface of the substrate, to be equivalently opposite to the first reticle, along the optical axis direction, in the optical path of the reflection illumination optical system, configured to be irradiated with the reflection illumination light, and have thereon a light-shielding pattern and a transmission pattern which are same shapes as those of the first reticle and whose arrangement direction is opposite to that of the first reticle;
   an equalizing circuit configured to perform gray scale value equalization by using a gray scale value output by the TDI sensor which received the pattern image of the substrate generated by irradiating the substrate with the reflection illumination light not passing through the first and second reticles;
   a distance change/move amount calculation circuit configured to calculate, in a state where the gray scale value equalization has been performed, a distance change/move amount of a relative distance, for focusing the pattern image of the substrate, between the substrate and the conjugate position of the TDI sensor by using a first derivative value of a gray scale value output by the TDI sensor which received the pattern image of the substrate generated by irradiating the substrate with the reflection illumination light having passed through the first and second reticles; and
   a drive mechanism configured to change/move the relative distance between the substrate and the conjugate position of the TDI sensor by using the distance change/move amount.

2. The apparatus according to claim 1, wherein the equalizing circuit performs the gray scale value equalization by adjusting gain and offset of the gray scale value output by the TDI sensor, by using gray scale data averaged in the direction of time integration of the TDI sensor.

3. The apparatus according to claim 2, wherein the gray scale data is generated by receiving the pattern image of the substrate by the TDI sensor in a state where the substrate is stopped.

4. The apparatus according to claim 1, further comprising:
   a derivative calculation circuit configured to calculate, in a state where the gray scale value equalization has been performed, the first derivative value of the gray scale value by using the gray scale value output by the TDI sensor which received a reticle pattern image of the substrate generated by irradiating the substrate with the reflection illumination light having passed through the first and second reticles.

5. The apparatus according to claim 4, further comprising:
   a height calculation circuit configured to calculate a height position of the substrate by using the first derivative value of the gray scale value in the state where the gray scale value equalization has been performed.

6. The apparatus according to claim 5, wherein the distance change/move amount calculation circuit calculates, as the distance change/move amount, a difference by subtracting the height position calculated, from a focusing height position where an image of the substrate is focused on the conjugate position of the TDI sensor.

7. The apparatus according to claim 1, wherein the distance change/move amount is calculated using a first derivative value of a gray scale value of a pattern end part at a side of the first reticle, and a first derivative value of a gray scale value of a pattern end part at a side of the second reticle.

8. A focusing method comprising:
   illuminating a substrate, on which a pattern is formed, with a reflection illumination light by using a reflection illumination optical system;
   receiving a pattern image of the substrate by a time delay integration sensor (TDI sensor) through an image forming optical system which forms the pattern image of the substrate;
   performing gray scale value equalization by using a gray scale value output by the TDI sensor which received the pattern image of the substrate generated by irradiating the substrate with the reflection illumination light;
   receiving the pattern image of the substrate by the TDI sensor generated by irradiating the substrate with the reflection illumination light having passed through a first reticle and a second reticle, in a state where the gray scale value equalization has been performed, by using the first and second reticles, the first reticle being arranged at a front side of a conjugate position of the TDI sensor facing a surface of the substrate, along an optical axis direction, in an optical path of the reflection illumination optical system, being configured to be irradiated with the reflection illumination light, and having thereon a light-shielding pattern whose end part is parallel with a direction of time integration of the TDI sensor, and a transmission pattern whose occupancy rate in an illumination region is larger than that of the light-shielding pattern, and the second reticle, being arranged at a back side of the conjugate position of the TDI sensor facing the surface of the substrate, to be equivalently opposite to the first reticle, along the optical axis direction, in the optical path of the reflection illumination optical system, being configured to be irradiated with the reflection illumination light, and having thereon a light-shielding pattern and a transmission pattern which are same shapes as those of the first reticle and whose arrangement direction is opposite to that of the first reticle;

calculating, in the state where the gray scale value equalization has been performed, a distance change/move amount of a relative distance, for focusing the pattern image of the substrate, between the substrate and the conjugate position of the TDI sensor by using a first derivative value of a gray scale value output by the TDI sensor which received the pattern image of the substrate generated by irradiating the substrate with the reflection illumination light having passed through the first and second reticles; and changing/moving the relative distance between the substrate and the conjugate position of the TDI sensor by using the distance change/move amount.

9. The method according to claim 8, wherein the gray scale value equalization is performed by adjusting gain and offset of the gray scale value output by the TDI sensor, by using gray scale data averaged in the direction of time integration of the TDI sensor.

10. A pattern inspection method comprising:
illuminating a substrate, on which an alignment pattern and a circuit pattern are formed, with a reflection illumination light by using a reflection illumination optical system;

receiving an alignment pattern image of the substrate by a time delay integration sensor (TDI sensor) through an image forming optical system which forms a pattern image of the substrate;

performing gray scale value equalization by adjusting a gain and offset by using a gray scale value output by the TDI sensor which received the alignment pattern image of the substrate generated by irradiating the substrate with the reflection illumination light;

arranging a first reticle, where a light-shielding pattern whose end part is parallel with a direction of time integration of the TDI sensor, and a transmission pattern whose occupancy rate in an illumination region is larger than that of the light-shielding pattern are formed, at a front side of a conjugate position of the TDI sensor facing a surface of the substrate, along an optical axis direction, in an optical path of the reflection illumination optical system, and also arranging a second reticle, where alight-shielding pattern and a transmission pattern which are same shapes as those of the first reticle and whose arrangement direction is opposite to that of the first reticle, at a back side of the conjugate position of the TDI sensor facing the surface of the substrate, to be equivalently opposite to the first reticle, along the optical axis direction, in the optical path of the reflection illumination optical system;

measuring, in a state where the gray scale value equalization has been performed by adjusting the gain and offset, a height position of the substrate by using a first derivative value of a gray scale value output by the TDI sensor which received the alignment pattern image of the substrate generated by irradiating the substrate with the reflection illumination light having passed through the first and second reticles;

acquiring a height position distribution of the substrate, based on the height position of the substrate; and inspecting the circuit pattern formed on the substrate while changing the height position of the substrate, based on the height position distribution.

* * * * *